(12) United States Patent
Peterson

(10) Patent No.: US 8,518,886 B2
(45) Date of Patent: Aug. 27, 2013

(54) CYTOPROTECTIVE THEREAPEUTIC AGENTS FOR THE PREVENTION OF REPERFUSION INJURY FOLLOWING ISCHEMIC STROKE

(75) Inventor: Darryl R Peterson, Barrington Hills, IL (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 0 days.

(21) Appl. No.: 13/089,697

(22) Filed: Apr. 19, 2011

(65) Prior Publication Data

US 2011/0312902 A1 Dec. 22, 2011

Related U.S. Application Data

(62) Division of application No. 11/479,776, filed on Jun. 30, 2006, now Pat. No. 7,956,037.

(60) Provisional application No. 60/731,564, filed on Oct. 27, 2005.

(51) Int. Cl.
*A61K 38/05* (2006.01)
(52) U.S. Cl.
USPC ...................... 514/17.7; 514/21.91
(58) Field of Classification Search
None
See application file for complete search history.

(56) References Cited

FOREIGN PATENT DOCUMENTS
WO WO/2004/026118 A2 4/2004

OTHER PUBLICATIONS

Plateel et al., "Hypoxia Increases the Susceptibility to Oxidant Stress and the Permeability of the Blood-Brain Barrier Endothelial Cell Monolayer", Journal of Neurochemistry, vol. 65, No. 5, 1995 pp. 2138-2145 XP000002657869 ISSN: 022-3042.
Bhattacharjee et al, "The Effects of the Na+/Ca++ Exchange Blocker on Osmotic Blood-Brain Barrier Disruption", Brain Research, vol. 900, No. 2, May 11, 2001, pp. 157-162, XP000002657870. ISSN: 0006-8993.
Agarwal, R. and Shukla. Potential role of cerebral glutathione in the maintenance of blood-brain barrier integrity in rat. Neurochem. Res. 24:1507-1514, 1999.
Betz, A.L. Transport of ions across the blood-brain barrier. Fed Proc. 45:2050-2054, 1986.
Betz, A.L., Firth, J.A. and Goldstein, G.W. Polarity of the blood-brain barrier: distribution of enzymes between the luminal and antiluminal membranes of brain capillary endothelial cells. Brain Res. 192, 17-28, 1980.
Betz, A.L. and Goldstein, G.W. Specialized properties and solute transport in brain capillaries. Ann. Rev. Physiol. 48:241-250, 1986.
Homma, M., Suzuki, H., Kusuhara, H., Naito, M., Tsuruo, T. and Sugiyama, Y. High-affinity efflux transport system for glutathione conjugates on the luminal membrane of a mouse brain capillary endothelial cell line (MBEC4). J. Pharmacol. Exp. Ther. 288:198-203, 1999.
Huai-Yun, H., Secrest, D.T., Mark, K.S., Carney, D., Brandquist, C., Elmquist, W.F. And Miller, D.W. Expression of multidrug resistance-associated protein (MRP) in brain microvessel endothelial cells. Biochem. Bioiphys. Res. Commmun. 243: 816-820, 1988.
Ishikawa T., The ATP-dependent glutathione S-conjugate export pump, Trends Biochem. Sci. 17:463-468, 1992.
Kannan, R., Kuhlenkamp, J.F., Jeandidier, E., Trinh, H., Ookhtens, M. and Kaplowitz, N. Evidence for carrier-mediated transport of glutathione across the blood-brain barrier in the rat. J. Clin. Invest. 85:2009-2013, 1990.
Kannan, R., Yi, J.R., Tang, D., Li, Y., Zlokovic, B.V. and Kaplowitz, N. Evidence for the existence of a sodium-dependent glutathione (GSH) transporter. J. Biol. Chem. 271:9754-9758, 1996.
Kannan, R., Mittur, A., Bao, Y., Tsuruo, T. and Kaplowitz, N. GSH transport in immortalized mouse brain endothelial cells: evidence for apical localization of a sodiuim-dependent GSH transporter. J. Neurochem. 73:390-399, 1999.
Keppler, D. and Konig, J. Expression and localization of the conjugate export pump encoded by the MRP2(cMEP/cMOAT) gene in liver. FASEB J. 11:509-516, 1997.
Kerper, L.E., Mokrzan, E.M., Clarkson, T.W. and Ballatori, N. Methylmercury efflux from brain capillary endothelial cells is modulated by intracellular glutathione but not ATP. Toxicol. Appl. Pharmacol. 141:526-531, 1996. Malo, et al., Analysis of kinetic data in transport studies: New insights from kinetic studies of Na+ -$_D$—glucose cotransport in human intestinal brush-border membrane vesicles using a fast sampling, rapid filtration apparatus, Journal of Membrane Biology vol. 122, No. 2/Jun. 1991, Springer New York.
Kusuhara, H., Suzuki, H. and Sugiyama, Y. The role of P-glycoprotein and canalicular multispecific organic anion transporter in the hepatobiliary excretion of drugs, J. Pharm. Sci. 87:1025-1040, 1998a. Meister, et al., Glutathione, Annual Review of Biochemistry, vol. 52: 711-760, Jul. 1983.
Kusuhara, H., Suzuki, H., Naito, M., Tsuruo, T. and Sugiyama, Y. Characterization of efflux transport of organic anions in a mouse brain capillary endothelial cell line. J. Pharmacol. Exp. Ther. 385:1260-65, 1998b. Mokrzan, et al., Methylmercury-thiol uptake into cultured brain capillary endothelial cells on amino acid system L, vol. 272, Issue 3, pp. 1277-1284, 1995 by American Society for Pharmacology and Experimental Therapeutics.
Lautier, D., Bailly, J.D., Demur, C., Herbert, J.M., Bousquet, C. and Laurent, G. Altered intracellular distribution of daunorubicin in immature acute myeloid leukemia cells. Int. J. Cancer 71:292-299, 1997. Oude Elferink RP, et al., Hepatobiliary secretion of organic compounds; molecular mechanisms of membrane transport, Biochim Biophys Acta, Jul. 17, 1995;1241(2):215-68.

(Continued)

*Primary Examiner* — Christina Bradley
(74) *Attorney, Agent, or Firm* — Joseph A. Fuchs; The Chicago Technology Law Group LLC

(57) ABSTRACT

The present invention relates generally to the use of γ-glutamyl antioxidants, particularly γ-glutamyl-cysteine, as cytoprotective agents to prevent reperfusion injury (i.e., hemorrhagic transformation) of the blood-brain barrier during reperfusion following an ischemic stroke. The γ-glutamyl antioxidants can be used alone or used in combination with an agent which inhibits the reverse movement of Na/Ca exchange in the blood-brain barrier such as 2-[2-[4-(4-nitrobenzyloxy)phenyl]ethyl]isothiourea methanesulphonate (KB-R7943).

9 Claims, 7 Drawing Sheets

(56) References Cited

OTHER PUBLICATIONS

Lee, W-J., Hawkins, R.A., Peterson, D.R. and Vina, J.R. Role of Oxoproline regulates amino acid transport across the blood-brain barrier. J. Biol. Chem. 271:19129-19133, 1996.

Loe, D.W., Stewart, R.K., Massey, T.E., Deeley, R.G. and Cole, S.P.C. ATP-dependent transport of aflatoxin B1 and its glutathione conjugates by the product of the multidrug resistance protein (MRP) gene. Mol. Pharmacol. 51:1034-1041, 1997.

Malo, C. and Berteloot, A. Analysis of kinetic data in transport studies: new insights from kinetic studies of $Na^+$-D-glucose cotransport in human intestinal brush-border membrane vesicles using a fast sampling, rapid filtration apparatus. J. Membr. Biol. 122:127-141, 1991.

Mares, V., Malik, R., Lisa, V., Sedo, A. Up-regulation of gamma-glutamyl transpeptidase (GGT) activity in growth perturbed C6 astrocytes, Mol. Brain Res. 136:75-80, 2005.

Meister, A. and Anderson, M.E. Glutathione. Ann. Rev. Biochem. 52, 711-760, 1983.

Mokrzan, E.M., Kerper, L.E., Ballatori, N. and Clarkson, T.W. Methylmercury-thiol uptake into cultured brain capillary endothelial cells on amino acid system L. J. Pharm. Exp. Ther. 272, 1277-1284, 1995.

Oude Elferink, R.P.J., Meijer, D.K.F., Kuipers, F., Jansen, P.L.M., Groan, A.K. and Groothuis, G.M.M. Hepatobiliary secretion of organic compounds, molecular mechanisms of membrane transport. Biochim. Biophys. Acta 1241, 215-268, 1995.

Peterson, D.R. and Hawkins, R.A. Isolation and behavior of plasma membrane vesicles made from cerebral capillary endothelial cells. In Pardridge, W. (ed.) *Introduction to the Blood-Brain Barrier*. Cambridge University Press, London, pp. 62-70, 1998. Partridge, et al., Introduction to the Blood-Brain Barrier, Methodology, Biology and Pathology, Cambridge University Press, 1998.

Peterson, D.R. and Hawkins, R.A. (2003) Transport studies using membrane vesicles. In Nag, S. (ed.) *The Blood-Brain Barrier*. Humana Press, Totowa, New Jersey, pp. 233-247, 2003. Peterson, et al., Transport Studies Using Membrane Vesicles, Springer Science & Business Media, Springer Protocols, vol. 89, pp. 233-247, 2003.

Sanchez Del Pino, M.M., Hawkins, R.A. and Peterson, D.R. et al., Neutral aAmino aAcid tTransport by the bBlood-brain bBarrier mMembrane vVesicle sStudies., The J. ournal of Biol.ogical Chem.istry, vol. 267:, No. 36, pp. 25951-25957, The American Society for Biochemistry and Molecular Biology, Inc., 1992.

Sanchez Del Pino, M.M., Hawkins, R.A. and Peterson, D.R. et al., Biochemical dDiscrimination between lLuminal and aAbluminal eEnzyme and tTransport aActivities of the bBlood-bBrain bBarrier. , J. ournal of Biol.ogical Chem.istry, vol. 270:, No. 25, pp. 14907-14912, The American Society for Biochemistry and Molecular Biology, Inc., 1995a.

Sanchez Del Pino, M.M., Peterson, D.R. and Hawkins, R.A. et al., Neutral aAmino aAcid tTransport cCharacterization of iIsolated lLuminal and aAbluminal mMembranes of the bBlood-bBrain bBarrier. , J. ournal of Biological Chem.istry, vol. 270:, No. 25, pp. 14913-14918, The American Society for Biochemistry and Molecular Biology, Inc., 1995b.

Skopicki, H.A., Fisher, K., Zikos, D., Flouret, G., Bloch, R., Kubillus, S. and Peterson, D.R. et al., Carrier-mediated transport of pyrryoglutamyl-histidine in renal brush border membrane vesicles. Am. J. Physiol., AJP—Cell Physiology, vol. 255:, Issue 6 C822-C827, 1988. American Physiological Society.

Sun, D., Lytle, C., and O'Donnell, M. et al., Astroglial cell-induced expression of Na-K-Cl cotransporter in brain microvascular endothelial cells. Am. J Physiol., AJP—Cell Physiology, vol. 269:, Issue 6 C1506-C1512, 1995., American Physiological Society.

Yamazaki, M., Kobayashi, K. and Sugiyama, Y. Primary active transport of pravastatin across the liver canalicular membrane in normal and mutant Eisai hyperbilirubinaemic rats. Biopharm. Drug Dispos. 17:645-59, 1996.

Yamazaki, et al., Primary active transport of pravastatin across the liver canalicular membrane in normal and mutant eisai hyperbilirubinaemic rats, Biopharm Drug Dispos., Nov. 1996;17(8): pp. 645-659.

Zhang, Y., Han, H., Elmquist, W.F. and Miller, D.W. et al., Expression of various multidrug resistance-associated protein (MRP) homologues in brain microvessel endothelial cells., Brain Research 876: (2000) 148-153, 2000. Elsevier Science B.V.

Zlokovic, B.V., Mackic, J.B., McComb, J.G., Weiss, M.H., Kaplowitz, N. and Kannan, R. BV, et al, Evidence for Transcapillary Transport of Reduced Glutathione in Vascular Perfused Guinea-pig Brian. , Biochem Biophys Res Commun. May 1994 20130; 201(1):401-408, 1994.

Lipton, "Ischemic Cell Death in Brain Neurons", Physiol. Rev., 1999, 79, (1431-1568).

Clark et al., "Efficacy of Antioxidant Therapies in Transient Focal Ischemia in Mice". Stroke, 2001, 32, 1000-1004.

Carrol et al., "Nuclear Factor-Nb Activation During Cerebral Reperfusion: Effect of Attenuation with N-acetylcysteine Treatment", Mol. Brain Res., 1998, 56, 186-191.

Khan et al., "Administration of N-acetylcysteine After Focal Cerebral Ischemia Protects Brain Inflammation in a Rat Model of Experimental Stroke", J. Neurosci. Res., 2004, 76, 519-527.

Anderson et al., "Glutathione Monoethyl Ester Provides Neuroprotection in a Rat Model of Stroke", Neurosci. Lett., 2004, 354, 163-165.

Park et al., "Dose-response Analysis of the Effect of 21-aminosteroid Tirilazad Mesylate (U-74006F) Upon Neurological Outcome and Ischemic Brain Damage in Permanent Focal Cerebral Ischemia", Grain Res., 1994, 645, 157-163.

Xue et al., "Tirilazad Reduces Cortical Infarction After Transient but not Permanent Focal Cerebral Ischemia in Rats", Stroke, 1992, 23, 894-899.

Yu et al., "Uric Acid Protects Neurons Against Excitotoxic and Metabolic Insults in Cell Culture, and Against Focal Ischemic Brain Injury in Vivo", J. Neurosci. Res., 1998, 53, 613-625.

Kilic et al., Pinealectomy Aggrabates and Melatonin Administration Attenuates Brain Damage in Focal Ischemia, J. Cereb. Blood Flow Metab., 1999, 19, 511-516.

Pei et al., "Pre-treatment with Melatonin Reduces Volume of Cerebral Infarction in a Permanent Middle Cerebral Artery Occlusion Stroke Model in the Rat", Neurosci. Lett., 2002, 318, 141-144.

Kilic et al., "Prophylactic Use of MelatoninProtects Against Focal Cerebral Ischemia in Mice: Role on Endothelin Converting Enzyme-1", J. Pineal. Res., 2004, 37, 247-251.

Cao et al., "a-Phenyl-tert-butyl-nitrone Reduces Cortical Infarct and Edema in Rats Subject to Focal Ischemia", Brain Res. 1994, 644, 267-272.

Zhao et al., "Delayed Treatment with the Spin Trap a-phenyl-n-tert-butyl Nitrone (PBN) reduces Infarct Size Following Transient Middle Cerebral Artery Occlusion in Rats", Acta Physiol., Scand., 1994, 152, 349-350.

Schultsa et al., "Facilitation of Postischemic Reperfusion with a-PBN: Assessment using NMR and Doppler Flow Techniques", Am. J. Physil., 1997, 272, H1986-H1995.

Zausinger et al., "Neurological Impairment in Rats After Transient Middle Cerebral Artery Occlusion: a Compartive Study Under Various Treatment Paradigms", Brain Res., 2000-, 863, 94-105.

Yang et al., "Neuroprotection by 2-h Postischemia Administration of Two Free Radical Scavengers, alpha-phenyl-n-terbutyl-n-nitrone (SPBN) in Rats Subjected to Focal Embolic Cerebral Ischemia", Exp Neurol. May 2000;163(1):39-45.

Kuroda et al., "Neuroprotective Effects of a Novel Nitrone, NXY-059, After Transient Focal Cerebral Ischemia in the Rat", J. Cereb. Bookd Flow Metab., 1999, 19, 778-787.

Sydserff et al., "Effect of NXY-059 on Infarct Volume After Transient or Permanent Middle Cerebral Artery Occlusion in the Rat; Studies on Dose, Plasma Concentration an Therapeutic Time Window", Br. J. Pharmacol., 2002, 135, 103-112.

Ginsberg et al., "Stilbazulenyl Nitrone, a Novel Antioxidant, is highly Neuroprotective in Focal Ischemia", Ann. Neurol., 2003, 54, 330-342.

Van Der Wrop et al., "Dietary Vitamin E level Affect Outcome of Permanent Focal Cerebral Ischemia in Rats", Stroke, 1998, 29, 1002-1006.

Mishima et al., "Vitamin E Isoforms Alpha-tocotrienol and Gamma-tocopherol Prevent Cerebral Infarction in Mice", Neurosci. Lett., 2003, 337, 56-60.

Garcia-Estrada et al., An alpha-lipoic acid-vitamin E Mixture reduces Postembolism Lipid Peroxidation, Cerebral Infarction, and Neurological Deficit in Rats. Neurosci. Res., 2003, 47, 219-224.

Huag et al., "Dehydroascorbic Acid, a Blood-brain Barrier Transmportable Form of Vitamin C, Mediates Potent Cerebroprotection in Experimental Stroke", Proc. Natl. Acad. Sci. USA, 2001, 98, 11720-11724.

Takamatsu et al., "Hydroxil Radical Generation After the Third Hour Following Ischemia Contributes to Brain Damage", Eur. J. Pharmocol., 1998, 352, 165-169.

Sinha et al., "Protective Effect of Resveratrol Against Oxidative Stress in Middle Cerebral Artery Occlusion Model of Stroke in Rats", Life Sci., 2002, 71, 655-655.

Andrabi et al., "Oxiresveratrol (trans-2,3V,4,5V-tetrahydroxystilbene) is Neuroprotective and Inhibits the Apoptotic Cell Death in Transient Cerebral Ischemia", Brain Res., 2004, 1017-, 98-107.

Misuno et al., "Inhibitory Effect of MCI-186, a Free Radical Scavenger on Cerebral Ischemia Following Rat Middle Cerebral Artery Occlusion", Gen. Pharm., 1998, 30, 575-578.

Shichinohe et al., "Neuroprotective Effects of the Free Radicle Scavenger Edaravone (MCI-186) in mice permanent focal brain Ischemia", Brain Res., 2004, 1029, 200-206.

The Edaravone Brain Infarction Study Group, "effect of a Novel Free Radical Scavenger, Edaravone (MCI-186), on Acute Brain Infarction, Placebo-controlled, Double-blind Study at Multicenters", Cerebrovasc. Dis., 2003, 15, 222-229.

Toyoda et al., "Free Radical Scavenger, Edaravone, in Stroke with Internal Carotid Artery Occlusion", J. Neurol. Sci., 2004, 221, 11-17.

Lee et al., "Sequential Combination Intravenous Recombinat Tissue Plasminogen Activator and Intra-Arterial Urokinase in Acute Ischemic Stroke", Am. J. Neuroradiology, 2004, 25, 1470-5.

Pilitsis et al., "Inhibition of Na-(+)/Ca(2+) Exchange by KB-R7943, a Novel Selective Antagonist, Attenuates Phosphoethanolamine and Free Fatty Acid Efflux in Rat Cerebral Cortex During Ischemia-Reperfusion Injury", Brain Res., 2001, 916, 192-8.

http://www.nlm.nih.gov/medlineplus/antioxidants.html.

Gilgum-Sherki et al., "Antioxidant Therapy in Acute Nervous System Injury: Current State", Pharm. Rev., 2002, 54, 271-84.

Drake et al., "Elevation of Brain Glutathione by—glutathione Analog, Against Peroxynitrite-induced Oxidative Stress", J. Nerosci., 2002, 68, 776-84.

Yamamoto et al., "Protective Actions of YM737, a new Flutathione Analog, Against Cerebral Ischemia in Rats", Res. Commun. Chem. Pathol. Pharmacol., 1993, 81.:221-32.

Stroke without drugs    Stroke with drugs

CYTOPROTECTIVE THEREAPEUTIC AGENTS FOR THE PREVENTION OF REPERFUSION INJURY FOLLOWING ISCHEMIC STROKE

CROSS-REFERENCE TO RELATED APPLICATION

This application is a divisional of U.S. patent application Ser. No. 11/479,776, filed Jun. 30, 2006, which claims priority from U.S. provisional Application Nos. 60/606,404 filed Jul. 1, 2005, and 60/731,564 filed Oct. 27, 2005, which are all incorporated in their entirety herein by reference and made a part hereof.

FEDERALLY SPONSORED RESEARCH OR DEVELOPMENT

This invention was made with United States government support under a Federal Work Study program. The United States government has certain rights in the invention.

BACKGROUND OF THE INVENTION

1. Field of the Invention

The present invention relates generally to the use of γ-glutamyl antioxidants, particularly γ-glutamyl-cysteine, as cytoprotective agents to prevent reperfusion injury (i.e., hemorrhagic transformation) of the blood-brain barrier during reperfusion following an ischemic stroke. The γ-glutamyl antioxidants can be used alone or used in combination with an agent which inhibits the reverse movement of Na/Ca exchange in the blood-brain barrier such as 2-[2-[4-(4-nitrobenzyloxy)phenyl]ethyl]isothiourea methanesulphonate (KB-R7943).

2. Background of the Invention

In the United States, someone experiences a stroke every minute, and dies from stroke-related complications approximately every three minutes. Strokes may be ischemic or hemorrhagic, but most are due to interrupted blood flow to the brain, resulting in hypoxia. Thus, the treatment for cerebral ischemia accompanying stroke includes therapies to re-establish blood flow. Surprisingly, reperfusion following cerebral ischemia may cause damage to the blood-brain barrier (Todd N V, Picozzi P, Crockard H A, and Russell R W R. Reperfusion after cerebral ischaemia: influence of duration of ischaemia. Stroke 17: 460-466, 1986) that can precipitate cerebral edema, hemorrhage, and ensuing neuropathologies. Thus, the cure may actually augment the disease. This appears to be especially true if reperfusion is delayed several hours, and current practice is to avoid reperfusing a patient after three hours of ischemia. Recent evidence has verified that using tissue plasminogen activator (t-PA) to dissolve clots is an effective treatment for stroke, if administered within the three hour interval. Unfortunately, statistics reveal that 95% of stroke victims are not treated in time. Thus, it is clear that finding a way to prevent the potential side-effects associated with thrombolysis would be a significant and life-saving contribution. The present invention discloses the use of γ-glutamyl antioxidants, particularly γ-glutamyl-cysteine, to prevent reperfusion injury (i.e., hemorrhagic transformation) of the blood brain barrier during thrombolytic treatment of ischemic stroke. The γ-glutamyl antioxidants can be used alone or used in combination with an agent which inhibits the reverse movement of Na/Ca exchange in the blood-brain barrier such as 2-[2-[4-(4-nitrobenzyloxy)phenyl]ethyl]isothiourea methanesulphonate (KB-R7943).

These and other aspects and attributes of the present invention will be discussed with reference to the following drawings and accompanying specification.

SUMMARY OF THE INVENTION

An embodiment of the present invention is a method for preventing blood-brain barrier reperfusion injury in a mammalian blood-brain barrier endothelial cell during reperfusion following ischemic stroke comprising administering an effective amount of a γ-glutamyl antioxidant to the subject. The blood-brain barrier endothelial cell is preferably a human cell. The γ-glutamyl antioxidant can be any antioxidant that is linked to a γ-glutamyl residue capable of reducing reactive oxygen species. A preferred γ-glutamyl antioxidant is γ-glutamyl cysteine. Other suitable γ-glutamyl antioxidants may include but are not limited to γ-glutamyl cysteine, γ-glutamyl methionine and γ-glutamyl d-methione. The γ-glutamyl antioxidant can be administered to a subject by intravenous injection into the subject. In an embodiment, the γ-glutamyl antioxidant is administered to the subject at a dose of about 400 mg/Kg. Preferably, the γ-glutamyl antioxidant is administered to the subject over a period of time. In another embodiment, the γ-glutamyl antioxidant is administered to the subject over a period of about one minute. In yet a further embodiment, the reperfusion following ischemic stroke is the result of a thrombolytic treatment, such as by administering tissue plasminogen activator or urokinase. In still another preferred embodiment, the method further comprises administering an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg.

Another embodiment of the present invention is a kit for use in preventing blood-brain barrier reperfusion injury in a mammalian blood-brain barrier endothelial cell during reperfusion following ischemic stroke comprising an effective amount of a γ-glutamyl antioxidant. Preferably, the blood-brain barrier endothelial cell is a human cell. The γ-glutamyl antioxidant can be any antioxidant that is linked to a γ-glutamyl residue capable of reducing reactive oxygen species. In a preferred embodiment, the γ-glutamyl antioxidant is γ-glutamyl cysteine. In another embodiment, the kit is suitable for injection into a subject over a period of time. An example of an effective amount is about 400 mg/Kg. In yet another preferred embodiment, the kit further comprises an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg.

Yet a further embodiment of the present invention is a method for preventing blood-brain barrier reperfusion injury in a mammalian blood-brain barrier endothelial cell during reperfusion following ischemic stroke comprising administering an effective amount of γ-glutamyl cysteine and an agent which inhibits reverse movement of Na/Ca exchange in the blood-brain barrier to the subject, such as but is not limited to, 2-[2-[4-(4-nitrobenzyloxy)phenyl]ethyl]isothiourea methanesulphonate (KB-R7943). Preferably, the blood-brain barrier endothelial cell is a human cell.

Still a further embodiment of the present invention is a kit for use in preventing blood-brain barrier reperfusion injury in a mammalian blood-brain barrier endothelial cell during reperfusion following ischemic stroke comprising an effective amount of γ-glutamyl cysteine and an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). Preferably, the blood-brain barrier endothelial cell is a human cell.

DETAILED DESCRIPTION OF THE INVENTION

Figure 1:
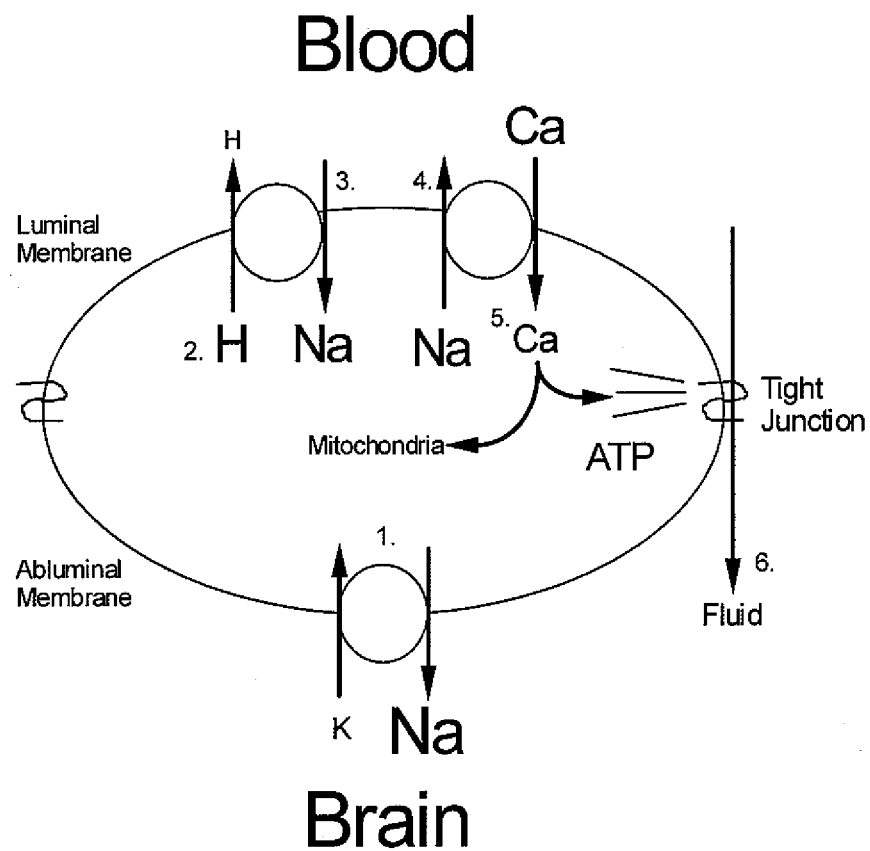
FIG. 1 is a schematic diagram showing a hypothetical model for ischemia-reperfusion damage to the blood-brain barrier.

While this invention is susceptible of embodiment in many different forms, there is shown in the drawings, and will be described herein in detail, specific embodiments thereof with the understanding that the present disclosure is to be considered as an exemplification of the principles of the invention and is not intended to limit the invention to the specific embodiments illustrated.

The present invention relates generally to the use of γ-glutamyl antioxidants as cytoprotective agents to prevent reperfusion injury (i.e., hemorrhagic transformation) of the blood-brain barrier during thrombolytic treatment of ischemic stroke. The γ-glutamyl antioxidants can be used alone or in combination with an agent which inhibits the reverse movement of Na/Ca exchange in the blood-brain barrier. An example of such an agent is 2-[2-[4-(4-nitrobenzyloxy)phenyl]ethyl]isothiourea methanesulphonate (KB-R7943). What is meant by "prevent reperfusion injury" or "prevention of reperfusion injury" in the present disclosure is that the cytoprotective agents, either alone or in combination with other agents, reduce the severity of the reperfusion injury. The reduction of the severity of the reperfusion injury by these agents can be partial, or these agents can completely eliminate the reperfusion injury.

A principal goal of treating cerebral ischemia associated with stroke is to re-establish blood flow to the brain (Del Zoppo G J, Von Kummer R, and Hammann G F. Ischaemic damage of brain microvessels: inherent risks for thrombolytic treatment in stroke. J Neurol Neurosurg Psychiatry 65: 1-9, 1998). It is now clearly established that delayed reperfusion may cause further damage to the blood-brain barrier (Gartshore G, Patterson J, and Macrae I M. Influence of ischemia and reperfusion on the course of brain tissue swelling and blood-brain barrier permeability in a rodent model of transient focal cerebral ischemia. Exp Neurol 147: 353-360, 1997; Todd N V, Picozzi P, Crockard H A, and Russell R W R. Reperfusion after cerebral ischaemia: influence of duration of ischaemia. Stroke 17: 460-466, 1986), increasing complications and morbidity. Damage to the blood-brain barrier is characterized by an increase in its permeability to solutes (Abbruscato T J and Davis T P. Combination of hypoxia/aglycemia compromises in vitro blood-brain barrier integrity. J Pharmacol Exp Ther 289: 668-675, 1999), accompanied by fluid influx from blood-to-brain, cerebral edema (Gartshore G, Patterson J, and Macrae I M. Influence of ischemia and reperfusion on the course of brain tissue swelling and blood-brain barrier permeability in a rodent model of transient focal cerebral ischemia. Exp Neurol 147: 353-360, 1997; Kuroiwa T, Shibutani M, and Okeda R. Blood-brain barrier disruption and exacerbation of ischemic brain edema after restoration of blood flow in experimental focal cerebral ischemia. Acta Neuropathol 76: 62-70, 1988), and eventually hemorrhage if cell structure deteriorates. Edema and hemorrhage, in turn, are associated with increased intracranial pressure and neural damage, possibly culminating in death.

Thus, the treatment for cerebral ischemia accompanying stroke includes therapies to re-establish blood flow, such as by administering tissue plasminogen activator (t-PA) or urokinase. Surprisingly, reperfusion following cerebral ischemia may cause damage to the blood-brain barrier (Todd N V, Picozzi P, Crockard H A, and Russell R W R. Reperfusion after cerebral ischaemia: influence of duration of ischaemia. Stroke 17: 460-466, 1986) that can precipitate cerebral edema, hemorrhage, and ensuing neuropathologies (Gartshore G, Patterson J, and Macrae I M. Influence of ischemia and reperfusion on the course of brain tissue swelling and blood-brain barrier permeability in a rodent model of transient focal cerebral ischemia. Exp Neurol 147: 353-360, 1997; Rosenberg G A, Estrada E Y, and J.E. D. Matrix metalloproteinases and TIMPs are associated with blood-brain barrier opening after reperfusion in rat brain. Stroke 29: 2189-2195, 1998; Todd N V, Picozzi P, Crockard H A, and Russell R W R. Reperfusion after cerebral ischaemia: influence of duration of ischaemia. Stroke 17: 460-466, 1986). Thus, the cure may actually augment the disease. This appears to be especially true if reperfusion is delayed several hours, and current practice is to avoid reperfusing a patient after three hours of ischemia (The National Institute of Neurological Disorders and Stroke rt-PA Stroke Study Group. Tissue plasminogen activator for acute ischemic stroke. N Engl J Med 333: 1581-1587, 1995).

Although relatively little is known about the mechanisms responsible for ischemia-reperfusion damage to the blood-brain barrier, it now appears that the process involves the accumulation of calcium, with ensuing cellular toxicity (Ikeda K, Nagashima T, Wu S, Yamaguchi M, and Tamaki N. The role of calcium ion in anoxia/reoxygenation damage of cultured brain capillary endothelial cells. Acta Neuochir Suppi (Wien) 70: 4-7, 1997). Evidence in our laboratory indicates that the process involves an increase in intracellular calcium concentration that serves as a signal to initiate a cascade of damaging effects. These data suggest that the initial elevation of intracellular calcium concentration is due to reverse movement of the Na/Ca exchanger during reperfusion, which effectively pumps calcium into the endothelial cells. This is stimulated by enhanced activity of the Na/H exchanger, which functions to remove hydrogen ions that accumulated during the ischemic phase, and reverses the electrochemical gradient for Na/Ca exchange by elevating intracellular sodium. The increased level of calcium in metabolically re-activated cells (in the presence of ATP) causes pathological changes associated with abnormal permeability of the barrier, including disruption of the cytoskeleton and tight junctions, mitochondrial dysfunction, and cellular damage. This sequence of events is illustrated in FIG. 1 which is a hypothetical model for ischemia-reperfusion damage to the blood-brain barrier. The numbers in the figure correspond to the sequence of events, as follows: 1) inhibition of the sodium pump during ischemia, causing accumulation of intracellular sodium and hydrogen ions; 2) stimulation of Na/H antiport due to outward movement of hydrogen ions during reperfusion; 3) obligatory inward movement of sodium during stimulated Na/H antiport, maintaining an elevated intracellular sodium concentration; 4) reverse activation of Na/Ca exchange, due to elevated intracellular sodium and a reversal of its electrochemical gradient during reperfusion; 5) inward movement and accumulation of calcium due to reverse activation of Na/Ca exchange; 6) calcium-mediated damage to the cytoskeleton, resulting in loosening of tight junctions and increased permeability of the barrier; alterations of mitochondrial function, causing cellular damage.

The blood-brain barrier is formed by polarized cerebral capillary endothelial cells that possess true tight junctions that impart a high electrical resistance (Betz A L, Firth J A, and Goldstein G W. Polarity of the blood-brain barrier: distribution of enzymes between the luminal and antiluminal membranes of brain capillary endothelial cells. Brain Res 192: 17-28, 1980; Reese T S and Karnovsky M J. Fine structural localization of a blood-brain barrier to exogenous peroxidase. J Cell Biol 34: 207-217, 1967). Adjacent cell-types (i.e., astrocytes, neurons, pericytes) interact with the capillaries to form what is now termed the "neurovascular unit". Due to the presence of tight junctions, for substances to pass between the blood and brain they must cross the luminal (blood-facing) and abluminal (brain-facing) plasma membranes of the endothelial cells (Bradbury M. The Concept of a Blood-Brain Barrier. New York: John Wiley and Sons, 1979). Selectivity is provided by the presence of specific transport proteins in each membrane domain (Bradbury M W B. The blood-brain barrier. Transport across the cerebral endothelium. Circ Res 57: 213-222, 1985). The barrier becomes leaky to solutes, accompanied by unusually large fluid fluxes, when its integrity is compromised. This may occur with loosening of tight junctions (Abbruscato T J and Davis T P. Combination of hypoxia/aglycemia compromises in vitro blood-brain barrier integrity. J Pharmacol Exp Ther 289: 668-675, 1999), or more extensive cell damage (Gartshore G, Patterson J, and Macrae I M. Influence of ischemia and reperfusion on the course of brain tissue swelling and blood-brain barrier permeability in a rodent model of transient focal cerebral ischemia. Exp Neurol 147: 353-360, 1997; Todd N V, Picozzi P, Crockard H A, and Russell R W R. Reperfusion after cerebral ischaemia: influence of duration of ischaemia. Stroke 17: 460-466, 1986). We have shown that reperfusion injury to the blood-brain barrier is associated with an elevation of intracellular calcium, apparently due to reverse activation of the Na/Ca exchanger. This rise in intracellular calcium is accompanied by alterations of the cytoskeletal/tight junctional complex, increased permeability to sucrose, and mitochondrial changes indicative of apoptosis.

Based upon evidence in other cell systems, the mechanisms for ischemia-reperfusion injury to the blood-brain barrier are probably complex. In general, cellular damage associated with ischemia and reperfusion has been ascribed to a cascade of events (DeKeyser J, Sulter G, and Luiten P G. Clinical trials with neuroprotective drugs in acute ischaemic stroke: are we doing the tight thing? Trends Neurosci 22: 535-540, 2001) including: 1) production of toxic oxidative agents, 2) activation of enzymes which cause membrane damage, 3) abnormal behavior of the cytoskeleton, 4) up-regulation of inflammatory processes, and 5) damage to mitochondria. Interestingly, each of these processes has been associated with an elevation of intracellular calcium (DeKeyser J, Sulter G, and Luiten P G. Clinical trials with neuroprotective drugs in acute ischaemic stroke: are we doing the tight thing? Trends Neurosci 22: 535-540, 2001), which appears to play a key role in cellular injury. Our results show that reperfusion injury to the blood-brain barrier is associated with a rise in intracellular calcium that is reduced by pharmacologically inhibiting reverse activation of the Na/Ca exchanger. The data indicate that elevated calcium alters the cytoskeleton, resulting in increased permeability characteristics of tight junctions. Furthermore, compelling evidence demonstrates damage to mitochondria, resulting in activation of caspase 3. This is highly suggestive of apoptosis, and reveals an additional dimension of reperfusion injury to the blood-brain barrier.

Ischemic stroke has been characterized by two phases of injury to the blood-brain barrier (Rosenberg G A. Matrix metalloproteinases in neuroinflammation. Glia 39: 279-291, 2002; Rosenberg G A, Estrada E Y, and J.E. D. Matrix metalloproteinases and TIMPs are associated with blood-brain barrier opening after reperfusion in rat brain. Stroke 29: 2189-2195, 1998) that remain enigmatic. The early phase occurs within hours of re-establishing blood flow, and is typified by a modest, reversible increase in blood-brain barrier permeability and cerebral edema (Rosenberg G A. Matrix metalloproteinases in neuroinflammation. Glia 39: 279-291, 2002; Rosenberg G A, Estrada E Y, and J. E. D. Matrix metalloproteinases and TIMPs are associated with blood-brain barrier opening after reperfusion in rat brain. Stroke 29: 2189-2195, 1998). Following an apparent recovery, the second delayed effect may involve severe damage to the barrier, resulting in hemorrhagic transformation and death (Rosenberg G A.

Matrix metalloproteinases in neuroinflammation. Glia 39: 279-291, 2002; Rosenberg G A, Estrada E Y, and J. E. D. Matrix metalloproteinases and TIMPs are associated with blood-brain barrier opening after reperfusion in rat brain. Stroke 29: 2189-2195, 1998). Based upon our data, we believe that the early phase is associated with a transient loosening of tight junctions in response to elevated intracellular calcium and alterations of the cytoskeleton. The second more devastating phase appears to coincide with mitochondrial damage and apoptosis. According to this interpretation, both phases are dependent upon the elevation of intracellular calcium that occurs during reperfusion, due to reverse activation of Na/Ca exchange. Thus, calcium is a central causative agent for injury, and each phase appears to be associated with the timing and compartmentalization of its respective calcium-dependent mechanisms.

Reperfusion injury associated with the cytoskeleton and tight junctions appears to include the following sequence of events: 1) binding of actin to a tight junctional protein, 2) contraction of actin and myosin in the presence of calcium, and 3) the production of stress conveyed to the junctional complex. We have shown that an alteration of the cytoskeleton in blood-brain barrier endothelial cells occurs during elevation of intracellular calcium, within the first 30 minutes of reperfusion. This is characterized by the formation of actin stress fibers, consistent with loosening of tight junctions (Abbruscato T J and Davis T P. Combination of hypoxia/aglycemia compromises in vitro blood-brain barrier integrity. J Pharmacol Exp Ther 289: 668-675, 1999). Furthermore, we have demonstrated that inhibition of calcium-activated myosin light chain kinase prevents this toxic effect. Myosin light chain kinase catalyzes the reaction between actin and myosin necessary for contraction. Since it has been shown that ischemia causes actin filaments to conjugate with ZO-1 (Tsukamoto T and Nigam S K. Tight junction proteins form large complexes and associate with the cytoskeleton in an ATP depletion model for reversible junction assembly. J Biot Chem 272: 16133-16139, 1997), a tight junctional protein, force generated by contraction of the cytoskeleton would be expected to weaken tight junctions and facilitate the formation of stress fibers. Each of these observations is consistent with the interpretation that early reperfusion injury to the blood-brain barrier is associated with the cytoskeleton and tight junctions.

Ischemia-reperfusion injury has been associated in several cell types with an alteration of mitochondria termed the mitochondrial permeability transition (MPT). This occurs when ischemic events are accompanied by an elevation of intracellular calcium in the presence of reactive oxygen species (ROS), that induces a change in permeability characteristics of the inner mitochondrial membrane (Halestrap A P. The mitochondrial permeability transition: its molecular mechanism and role in reperfusion injury. Biochem Soc Symp 66: 181-203, 1999). This change in permeability is associated with release of cytochrome c, and results in uncoupling of oxidative phosphorylation. The reduction in ATP production initiates activation of caspases, including caspase 3, that has been associated with apoptosis (Mayer B and Oberbauer R. Mitochondrial regulation of apoptosis. NIPS 18: 89-94, 2003). Apoptosis is a pattern of programmed cell death, characterized by a regular fragmentation of nuclear DNA that is measured by the so-called TUNEL assay. The apoptotic process results in cell damage, indicated by release of cytoplasmic lactate dehydrogenase (LDH). We have shown that activation of caspase 3 is delayed in blood-brain barrier cells exposed to ischemic conditions, occurring at 24 hours of reperfusion, but not after 3 hours of reperfusion. This pattern of delayed, potentially damaging toxicity is typical of what occurs during phase 2 of reperfusion injury to the blood-brain barrier.

It is known that ischemia-reperfusion injury to a variety of cell types involves an increase in intracellular calcium concentration (Ikeda K, Nagashima T, Wu S, Yamaguchi M, and Tamaki N. The role of calcium ion in anoxia/reoxygenation damage of cultured brain capillary endothelial cells. Acta Neuochir Suppl (Wien) 70: 4-7, 1997) that serves as a signal to initiate a cascade of damaging effects (Orrenius S, Ankarcrona M, and Nicotera P. Mechanisms of calcium-related cell death. Adv Neurol 71: 137-151, 1996). We hypothesized that the initial elevation of intracellular calcium concentration in the blood-brain barrier is associated with reverse movement of the Na/Ca exchanger during reperfusion, which effectively pumps calcium into the endothelial cells. Accordingly, this is stimulated by enhanced activity of the Na/H exchanger, which functions to remove hydrogen ions that accumulated during the ischemic phase, and reverses the electrochemical gradient for Na/Ca exchange by elevating intracellular sodium. The proposed sequence of events is as follows: 1) ischemia causes intracellular sodium concentration to increase, due to lowered ATP production and reduced activity of the sodium pump; 2) a diminished inwardly directed electrochemical gradient for sodium permits diminished Na/H exchange activity and thus causes an accumulation of hydrogen ions within the cells; 3) during reperfusion a large outwardly directed hydrogen ion gradient is created, driving the Na/H exchanger, which stimulates sodium uptake by the cells; 4) an elevated intracellular sodium concentration causes the Na/Ca exchanger to run in reverse, creating an unusually high level of intracellular calcium; 5) the increased level of calcium in metabolically re-activated cells (presence of ATP) causes pathological changes associated with abnormal permeability of the barrier, including disruption of the cytoskeleton and tight junctions, as well as damage to mitochondria.

Based on the above hypothesis, calcium-mediated injury to tight junctions and mitochondria in blood-brain barrier cells can be treated pharmacologically by preventing a rise in intracellular calcium during reperfusion, and/or replenishing antioxidant lost during ischemia. In the present invention, we disclose that providing antioxidants during ischemia/reperfusion assists in preventing the progression of mitochondrial injury to apoptosis. Effectively replenishing lost antioxidants at the time of reperfusion could serve as a reasonable therapeutic strategy. It has been shown that loss of GSH in the blood-brain barrier during ischemia is associated with injury (Muruganandam A, Smith C, Ball R, Herring T, and Stanimirovic D. Glutathione homeostasis and leukotriene-induced permeability in human blood-brain barrier endothelial cells subjected to in vitro ischemia. Acta Neurochir Suppl 76: 29-34, 2000). Since GSH synthesis requires energy, and carriers are present in blood-brain barrier cells allowing it to leave passively (Peterson D R, Rambow J, Sukowski E J, and Zikos D. Glutathione transport by the blood-brain barrier. FASEB J 13: A709, 1999), one would expect GSH to become depleted during ischemia. GSH can be replenished by administering a glutathione-related antioxidant, such as but is not limited to glutathione (GSH), N-acetylcysteine (NAC), and a γ-glutamyl thiol such as γ-glutamyl-cysteine (γ-Glu-Cys). In addition, further prevention of reperfusion injury can be accomplished by co-administration of an agent which inhibits the reverse movement of Na/Ca exchange in the blood-brain barrier such as 2-[2-[4-(4-nitrobenzyloxy)phenyl]ethyl] isothiourea methanesulphonate (KB-R7943). What is meant by "co-administration" is that the administration of the agents can be simultaneous or in tandem in which one agent is administered followed by the other. Our data are consistent with the interpretation that γ-glutamyl antioxidants alone or in combination with an agent which inhibits the reverse movement of Na/Ca exchange in the blood-brain barrier, such as 2-[2-[4-(4-nitrobenzyloxy)phenyl]ethyl]isothiourea methanesulphonate (KB-R7943), prevent reperfusion injury of the blood-brain barrier endothelial cells following an ischemic stroke. Although the discovery of the use of these agents is based on the above-described hypothesis, the invention of the present disclosure should not be bound by any specific theory or hypothesis.

For in vivo administrations, the γ-glutamyl antioxidants can be injected intravenously at a dose of, for example, about 400 mg/Kg over 1 minute, at the time of reperfusion. However, of the glutathione-related antioxidants, GSH or NAC when infused intravenously may not be taken up by blood-brain endothelial cells quickly enough to completely restore intracellular GSH in a timely fashion. We have shown that a passive carrier is present in the luminal membrane of blood-brain barrier cells that normally facilitates cell-to-blood movement of GSH down its electrochemical gradient (Peterson D R, Rambow J, Sukowski E J, and Zikos D. Glutathione transport by the blood-brain barrier. FASEB J 13: A709, 1999). With intracellular GSH depletion and relatively high levels of the antioxidant added to the blood, sufficient inward movement may be accomplished. Although NAC has been shown to function in a variety of cell types as a GSH precursor with cytoprotective effects (Anderson M E. Glutathione and glutathione delivery compounds. In: Advances in Pharmacology. New York: Academic Press, 1997, p. 65-78), very little is known about its transport mechanisms by cells. Of concern is whether NAC must be deacetylated prior to uptake by blood-brain barrier cells. γ-glutamyl thiols like γ-glutamyl cysteine are potential cytoprotective agents under energy-depleted conditions, because they should enter passively and utilize less energy to form glutathione (Anderson M E. Glutathione and glutathione delivery compounds. In: Advances in Pharmacology. New York: Academic Press, 1997, p. 65-78). Furthermore, since they possess sulfhydryl groups, they are antioxidants by themselves. Other similar cytoprotective antioxidants can also be used (e.g., GSH monoester and γ-glutamyl-dipeptides containing a reactive sulfur such as γ-glutamyl-cystine, γ-glutamyl-methionine, γ-glutamyl-d-methionine and the like). Cytoprotective γ-glutamyl dipeptides containing a reactive sulfur can further be conjugated to other molecules such as NAC or another therapeutic agent.

These antioxidants can be administered alone, or more preferably, they can be administered in combination with an agent which inhibits the reverse movement of Na/Ca exchange in the blood-brain barrier. An example of such an agent is 2-[2-[4-(4-nitrobenzyloxy)phenyl]ethyl]isothiourea methanesulphonate (KB-R7943, by Pharmaceutical Research Laboratories, Kanebo Ltd., Osaka, Japan). Several studies in cardiac and renal tissues have shown that KB-R7943 inhibits Na/Ca exchange, and that it has a greater affinity for suppressing movement in the reverse direction (Iwamoto T, Watano T, and Shigekawa M. A novel isothiourea derivative selectively inhibits the reverse mode of Na/Ca exchange in cells expressing NCX1. J Biol Chem 271: 22391-22397, 1996). Furthermore, KB-R7943 has been shown to be cytoprotective under conditions of ischemia and reperfusion in both the heart and kidney (Kuro T, Kobayashi Y, Takaoka M, and Matsumura Y. Protective effect of KB-R7943, a novel Na/Ca exchange inhibitor, on ischemic acute renal failure in rats. J Pharmacol 81: 247-251, 1999; Nakamura A, Harada K, Sugimoto H, Nakajima F, and Nishimura N. Effects of KB-R7943, a novel Na/Ca inhibitor, on myocardial ischemia/reperfusion injury. Folia Pharmacol Jpn 111: 105-115, 1998).

An embodiment of the present invention is a method for preventing blood-brain barrier reperfusion injury in a mammalian blood-brain barrier endothelial cell during reperfusion following ischemic stroke comprising administering an effective amount of a γ-glutamyl antioxidant to the subject. The blood-brain barrier endothelial cell is preferably a human cell. The γ-glutamyl antioxidant can be any antioxidant that is linked to a γ-glutamyl residue capable of reducing reactive oxygen species. A preferred γ-glutamyl antioxidant is γ-glutamyl cysteine. Other suitable γ-glutamyl antioxidants may include but are not limited to γ-glutamyl cystine, γ-glutamyl methionine, and γ-glutamyl d-methione. The γ-glutamyl antioxidant can be administered to a subject by intravenous injection into the subject. In an embodiment, the γ-glutamyl antioxidant is administered to the subject at a dose of about 400 mg/Kg. Preferably, the γ-glutamyl antioxidant is administered to the subject over a period of time. In another embodiment, the γ-glutamyl antioxidant is administered to the subject over a period of about one minute. In yet a further embodiment, the reperfusion following ischemic stroke is the result of a thrombolytic treatment, such as by administering tissue plasminogen activator or urokinase. In still another preferred embodiment, the method further comprises administering an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg.

Another embodiment of the present invention is a kit for use in preventing blood-brain barrier reperfusion injury in a mammalian blood-brain barrier endothelial cell during reperfusion following ischemic stroke comprising an effective amount of a γ-glutamyl antioxidant. Preferably, the blood-brain barrier endothelial cell is a human cell. The γ-glutamyl antioxidant can be any antioxidant that is linked to a γ-glutamyl residue capable of reducing reactive oxygen species. In a preferred embodiment, the γ-glutamyl antioxidant is γ-glutamyl cysteine. In another embodiment, the kit is suitable for injection into a subject over a period of time. An example of an effective amount is about 400 mg/Kg. In yet another preferred embodiment, the kit further comprises an agent which inhibits reverse movement of Na/Ca exchange in the blood-brain barrier, such as but is not limited to 2-[2-[4-(4-nitrobenzyloxy)phenyl]ethyl]isothiourea methanesulphonate (KB-R7943). An example of an effective amount of KB-R7943 is 10 mg/Kg.

Yet a further embodiment of the present invention is a method for preventing blood-brain barrier reperfusion injury in a mammalian blood-brain barrier endothelial cell during reperfusion following ischemic stroke comprising administering an effective amount of γ-glutamyl cysteine and an agent which inhibits reverse movement of Na/Ca exchange in the blood-brain barrier to the subject, such as but is not limited to, 2-[2-[4-(4-nitrobenzyloxy)phenyl]ethyl]isothiourea methanesulphonate (KB-R7943). Preferably, the blood-brain barrier endothelial cell is a human cell.

Still a further embodiment of the present invention is a kit for use in preventing blood-brain barrier reperfusion injury in a mammalian blood-brain barrier endothelial cell during reperfusion following ischemic stroke comprising an effective amount of γ-glutamyl cysteine and an agent which inhibits reverse movement of Na/Ca exchange in the blood-brain barrier, such as but is not limited to 2-[2-[4-(4-nitrobenzyloxy)

phenyl]ethyl]isothiourea methanesulphonate (KB-R7943). Preferably, the blood-brain barrier endothelial cell is a human cell.

EXAMPLES

Example 1

Culturing Blood-brain Barrier Cells

Cultured blood-brain barrier cells can be used as an in vitro cellular model to confirm that Na/Ca exchange may operate in the reverse direction under conditions simulating reperfusion, following transient ischemia. Cerebral capillary endothelial cells are isolated from bovine brain by the method of Meresse et al. (Meresse S, Dehouck M-P, Delmore P, Bensaid M, Tauber J-P, Delbart C, Fruchart J-C, and Cecchelli R. Bovine brain endothelial cells express tight junctions and monoamine oxidase activity in long-term culture. J Neurochem 53: 1363-1371, 1989), or purchased from Cell Systems Corporation (Kirkland, Wash). Cells are grown and maintained (up to passage 5) on collagen type I- and fibronectin-coated tissue culture flasks in Eagle's minimal essential medium supplemented with 10% fetal bovine serum (Rubin L L, Hall D E, Porter S, Barbu K, Cannon C, Homer H C, Janatpour M, Liaw C W, Manning K, Morales J, Tanner L I, Tomaselli K J, and Bard F. A cell culture model of the blood-brain barrier. J Cell Biol 115: 1725-1735, 1991; Sun D, Lytle C, and O'Donnell M. Astroglial cell-induced expression of Na—K—Cl cotransporter in brain microvascular endothelial cells. Am J Physiol 269: C1506-C1512, 1995). To form a polarized endothelium, cells are seeded on cluster plate inserts and incubated in the presence of an astrocyte conditioned medium supplemented with cAMP, as previously described (Audus K L, Rose J M, Wang W, and Borchardt R. Brain microvessel endothelial cell culture systems. In: Introduction to the Blood-Brain Barrier, edited by Pardridge W M. Cambridge: Cambridge University Press, 1998, p. 86-93; Rubin L L, Hall D E, Porter 8, Barbu K, Cannon C, Homer H C, Janatpour M, Liaw C W, Manning K, Morales J, Tanner L I, Tomaselli K J, and Bard F. A cell culture model of the blood-brain barrier. J Cell Biol 115: 1725-1735, 1991). Endothelial cells may be identified by staining for factor VIII-related antigen, and the absence of a reaction product for glial fibrillary acidic protein. In addition, measurements of γ-glutamyl transpeptidase and electrical resistance (see below) are made to indicate differentiation (DeBault L E. γ-glutamyl transpeptidase induction mediated by glial foot process-to-endothelium contact in co-culture. Brain Res 220: 432-435, 1981; Rubin L L, Hall D E, Porter S, Barbu K, Cannon C, Homer H C, Janatpour M, Liaw C W, Manning K, Morales J, Tanner L I, Tomaselli K J, and Bard F. A cell culture model of the blood-brain barrier. J Cell Biol 115: 1725-1735, 1991. Several studies have shown that cultured brain capillary endothelial cells behave as a functional blood-brain barrier in vitro (Beucicmann C T and Galla H-J. Tissue culture of brain endothelial cells-induction of blood-brain barrier properties by brain factors. In: Introduction to the blood-brain barrier, edited by Pardridge W M. Cambridge: Cambridge University Press, 1998, p. 79-85). This model can to be used to simulate blood-brain barrier function with clinical applications (Rubin L L, Hall D E, Porter S, Barbu K, Cannon C, Homer H C, Janatpour M, Liaw C W, Manning K, Morales J, Tanner L I, Tomaselli K J, and Bard F. A cell culture model of the blood-brain barrier. J Cell Biol 115: 1725-1735, 1991).

Example 2

Ischemia-reperfusion Protocol Using Cultured Cells

Cultured blood-brain barrier cells can be exposed to conditions simulating ischemia and reperfusion, by a method similar to that reported in the literature (Ikeda K, Nagashima T, Wu S, Yamaguchi M, and Tarnaki N. The role of calcium ion in anoxia/reoxygenation damage of cultured brain capillary endothelial cells. Acta Neuochir Suppl (Wien) 70: 4-7, 1997). The precise composition of the incubation medium varies, depending upon the experimental protocols. In general, however, cells are incubated at 37° C. first in an ischemic medium (without glucose, pH 6.8) equilibrated with an atmosphere of 95% $N_2$ and 5% $CO_2$, followed by simulated reperfusion in a control medium (5.6 mM glucose, pH 7.4) equilibrated with room air and 5% $CO_2$. Typical incubation media are as follows: (control) 114 mM NaCl, 81 mM $Na_2HPO_4$, 0.5 mM $MgCl_2$, 0.9 mM $CaCl_2$, 5.6 mM glucose, and 24 mM $NaHCO_3$, pH 7.4; (ischemic) 133.4 mM NaCl, 4.1 mM $Na_2HPO_4$, 4.1 mM $KH_2PO_4$, 12.6 mM Hepes, 2.4 mM Tris, 0.5 mM $MgCl_2$, 0.9 mM $CaCl_2$, and 6 mM $NaHCO_3$, pH 6.8. To provide a constant environment, the cells are maintained in sealed chambers (Billups-Rothenberg, Calif.) that have been pre-equilibrated to the desired atmospheric conditions during the course of the experiment.

Example 3

Evidence that Intracellular Sodium Concentration in Blood-brain Barrier Endothelial Cells is Increased During Ischemia, and Remains Elevated During Reperfusion Due to Na/H Exchange Cultured bovine blood-brain barrier endothelial cells were exposed to conditions simulating ischemia and reperfusion as described in Example 2. Sodium fluorescence was measured in cultured bovine blood-brain barrier endothelial cells under the following conditions: 1) control (120 minutes), 2) simulated ischemia (120 minutes), 3) simulated ischemia (90 minutes) followed by simulated reperfusion (30 minutes), 4) simulated ischemialreperfusion (90/30 minutes), in the presence of an inhibitor (dimethylamiloride, 100 μM) of Na/H exchange.

The experimental protocol included exposing the cultured blood-brain barrier cells to the following treatments: 1) control conditions in the presence of oxygen and glucose, pH 7.4. 2) ischemia (no oxygen or glucose, pH 6.8), 3) ischemia followed by reperfusion (oxygen and glucose added back, pH 7.4), 4) ischemia followed by reperfusion in the presence of 100 μM N,N dimethyl amiloride (DMA), an inhibitor of Na/H exchange. After the cells in each of the four Petri dishes were treated to the respective environments, their sodium levels were determined using fluorescence techniques.

In preparation for the experiments, the control and ischemic bicarbonate buffers were sterile filtered, transferred to empty Petri dishes, and pre-equilibrated overnight in sealed chambers containing air plus 5% $CO_2$, or $N_2$ plus 5% $CO_2$, respectively. The next morning each chamber was re-gassed and placed in a water bath at room temperature for the duration of the experiment.

Prior to treatment, the cells were preloaded with Sodium Green, a fluorescent probe used to measure intracellular sodium concentration. First, the growth medium was removed from the cells, after which they were washed with 2 ml sterile (control) bicarbonate buffer. Each dish was then treated with 2 ml of a 5 μM Sodium Green solution. The working solution was prepared by mixing 50 μg Sodium Green with 6.48 μl dimethyl sulfoxide (DMSO) and 6.48 ml of pre-equilibrated (control) bicarbonate buffer. All 4 sets of cells were preloadeded in the air plus 5% $CO_2$ chamber for 30 minutes in the dark, because Sodium Green is light sensitive.

Following loading of the fluorescent probe, the control cells were washed and treated with 2 ml of normal bicarbonate buffer. They were then placed in the chamber with air plus 5% $CO_2$ for 90 minutes. The other 3 sets of cells were washed, treated with ischemic bicarbonate buffer, and placed in the chamber with $N_2$ plus 5% $CO_2$ for 90 minutes. As indicated above, one of these was treated under ischemic conditions in the presence of 100 μM N,N dimethyl amiloride, an inhibitor of the Na/H antiporter.

After 90 minutes of treatment, the incubation medium in each dish was replaced with fresh material. For the two ischemic treatments to be "reperfused" (i.e., ischemia/reperfusion and ischemia/reperfusion plus inhibitor), the medium was replaced with control bicarbonate buffer, and the dishes were transferred to the air plus 5% $CO_2$ chamber. This was followed by an additional 30 minutes of treatment.

After 30 minutes, the Petri dishes were removed from both chambers and placed on ice. The bicarbonate buffer was removed, and the cells were washed with Mikes PBS (10 mM $Na_2HPO_4$, 0.9% NaCl, pH of 7.5) and treated for an additional 30 minutes with 2 ml of 2% PFA solution, pH 8, on ice. The cells were then washed again 3× with 2 ml Mikes PBS solution. The four coverslips from each petri dish were mounted onto a microscope slide using PVA-DABCO mountant. Thus, there were a total of four slides with 4 coverslips on each slide. These were placed in a dark box (since Sodium Green is light sensitive) in the refrigerator and stored for three days, until the slides were dry enough to visualize.

After three days of storage in the refrigerator, the cells were examined with a Nikon fluorescence microscope. To quantify sodium fluorescence, digital pictures were taken at a magnification of 40× under oil immersion, using a FITC filter. Four pictures were taken from each coverslip, and four coverslips represented each treatment. Fifty random cells from each of the four treatments were measured for fluorescence, using a computer-assisted morphometric program called Metamorph. Cellular fluorescence was quantified as a function of its area. The following settings were used to measure Sodium Green fluorescence: red 0.731, green 0.933, blue 10.044, and gain 16.

Figure 2:
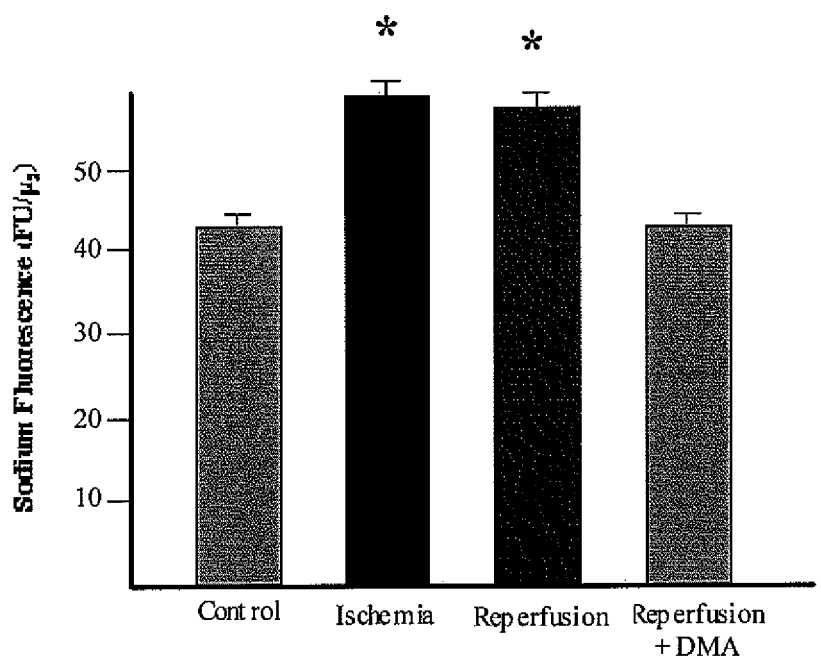
FIG. 2 is the data showing that a significant (*, $P<0.05$) increase in intracellular sodium concentration is observed during ischemia, and remains elevated during reperfusion in cultured blood-brain barrier endothelial cells. Inhibition of Na/H exchange inhibits ($P<0.05$) the rise in intracellular sodium observed following ischemia/reperfusion.

The data, displayed in FIG. 2, show that a significant (*, P<0.05) increase in intracellular sodium concentration is observed during ischemia, and remains elevated during reperfusion. Inhibition of Na/H exchange by 100 μM of dimethylamiloride (DMA) inhibits (P<0.05) the rise in intracellular sodium observed following ischemia/reperfusion. Values are mean±SD.

Example 4

Evidence that Elevated Intracellular Sodium and Reverse Activation of Na/Ca Exchange Contribute to a Rise in Intracellular Calcium During Reperfusion Following Ischemia Calcium fluorescence (FIG. 3) was measured in cultured bovine blood-brain barrier endothelial cells under conditions similar to those used for FIG. 2: 1) control, 2) simulated ischemia, 3) simulated ischemia followed by simulated reperfusion, 4) simulated ischemia/reperfusion, in the presence of an inhibitor (dimethylamiloride, 100 μM) of Na/H exchange (upper panel), or an inhibitor (KB-R 7943, 20 μM) of the reverse movement of Na/Ca exchange (lower panel). Intracellular calcium was quantified in cultured blood-brain barrier cells by using a fluorescent probe and confocal laser microscopy (Ikeda K, Nagashima T, Wu S, Yamaguchi M, and Tamaki N. The role of calcium ion in anoxia/reoxygenation damage of cultured brain capillary endothelial cells. Acta Neuochir Suppl (Wien) 70: 4-7, 1997). Measurements were made under conditions of ischemia and reperfusion, as described in Example 2. Prior to incubation, the media were sterile filtered and pre-equilibrated overnight in sealed chambers containing air plus 5% $CO_2$ (control) or 95% $N_2$ plus 5% $CO_2$ (ischemia). The next morning each chamber was re-gassed and placed in a water bath at room temperature for the duration of the experiment. The cells were preloaded for 30 minutes (25) with Fluo-4 (Molecular Probes), a fluorescent calcium probe. Preloaded cells were washed with bicarbonate buffer and treated under conditions of ischemia and reperfusion, as described in Example 2. Following treatment, the tissue was excited at 494 nm, and fluorescence was measured at the same wavelength to determine bound calcium, since the probe is non-fluorescent when calcium is free. Calcium concentration was quantified in 50 randomly chosen (computer-assisted) cells, representing each treatment.

Figure 3:
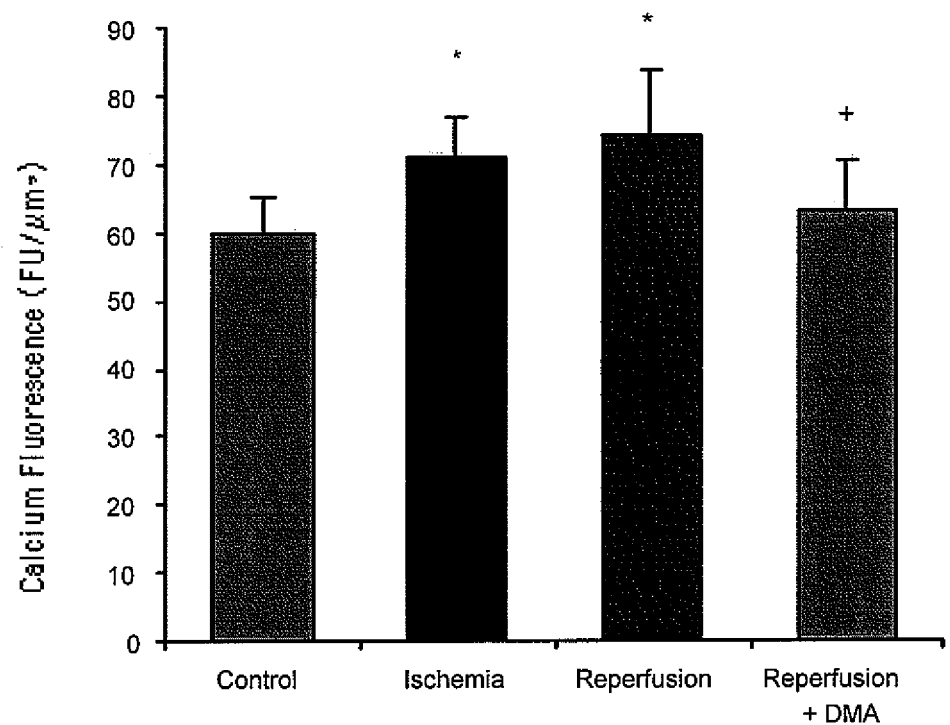
FIG. 3 is the data showing that a significant (*, $P<0.05$) increase in intracellular calcium concentration is observed during ischemia, and remains elevated during reperfusion in cultured blood-brain barrier cells. Inhibition of Na/H exchange (upper panel) or the reverse movement of Na/Ca exchange (lower panel) inhibits (+, $P<0.05$) the rise in intracellular calcium observed following ischemia/reperfusion.
Figure 3:
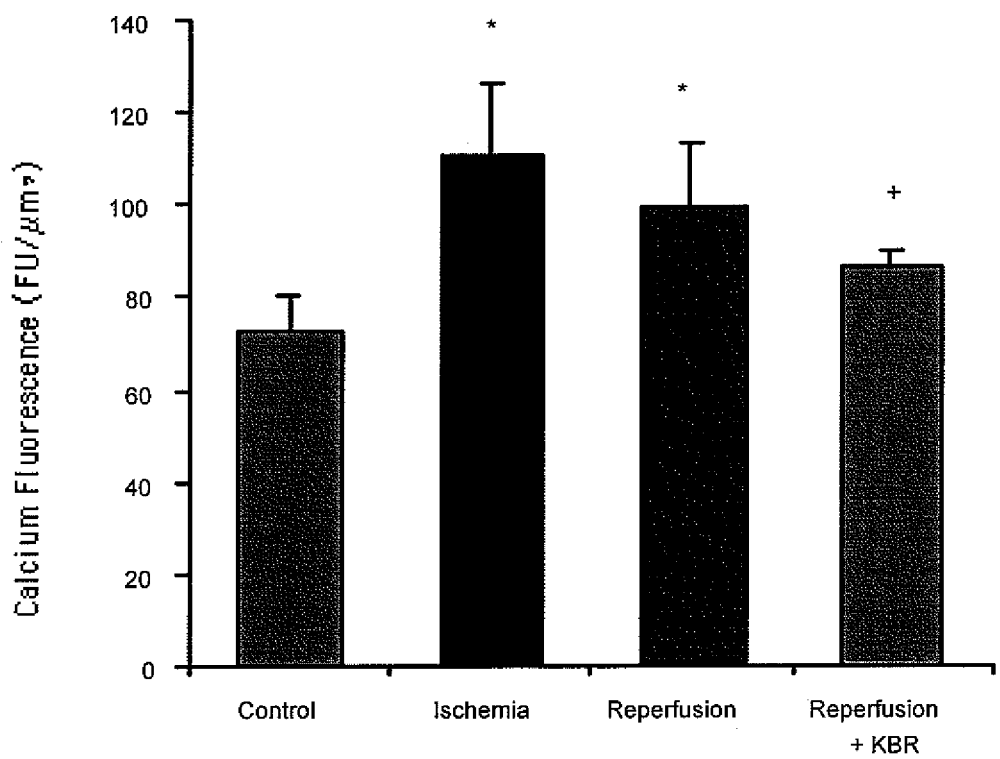

The data, shown in FIG. 3, show that a significant (*, P<0.05) increase in intracellular calcium concentration is observed during ischemia, and remains elevated during reperfusion. Inhibition of Na/H exchange by 100 μM of DMA (upper panel) or the reverse movement of Na/Ca exchange by 20 μM of KB-R7943 (KBR) (lower panel) inhibits the rise in intracellular calcium observed following ischemia/reperfusion (+, P<0.05). Values are mean±SD. N=50 observations. This supports the working hypothesis that activation of Na/H exchange and reverse movement of Na/Ca exchange during reperfusion following transient ischemia elevates intracellular calcium.

Example 5

Evidence that Activation of Na/H Exchange During Ischemia/Reperfusion Results in Elevated Intracellular Calcium Concentration that in Turn Initiates Mitochondrial Damage and Caspase 3 Activation Caspase 3 activity was measured in cultured bovine blood-brain barrier endothelial cells under control conditions (24.5 hours), simulated ischemia (24.5 hours), or ischemia followed by reperfusion (I/Rep) as described in Example 2. The cells were exposed to 30 minutes of ischemic conditions, followed by 24 hours of reperfusion. Once again, N,N dimethyl amiloride (100 μM) served as an inhibitor of Na/H antiport. Z-VAD-FMK (50 mM), a specific inhibitor of caspase 3 activity, was used as an internal control. The cells were co-treated with inhibitors during the entire duration of ischemia and reperfusion. Three wells were incubated per treatment. Following treatment, each plate was placed on ice, the bicarbonate buffer was removed, and the cells were washed with 2 ml Mikes PBS, pH 7.4. The PBS was removed, and 100 μl of lysis buffer was added to each well. Next, cells were scraped off the wells and transferred to 2 ml Eppendorf tubes.

Lysed material from each well was incubated for 4 hours at room temperature with colorimetric substrates for caspase 3. Absorbance at 405 nm was quantified with a Tecan/Genios plate reader and converted to units of activity (A/50 μg protein/time of incubation).

Figure 4:
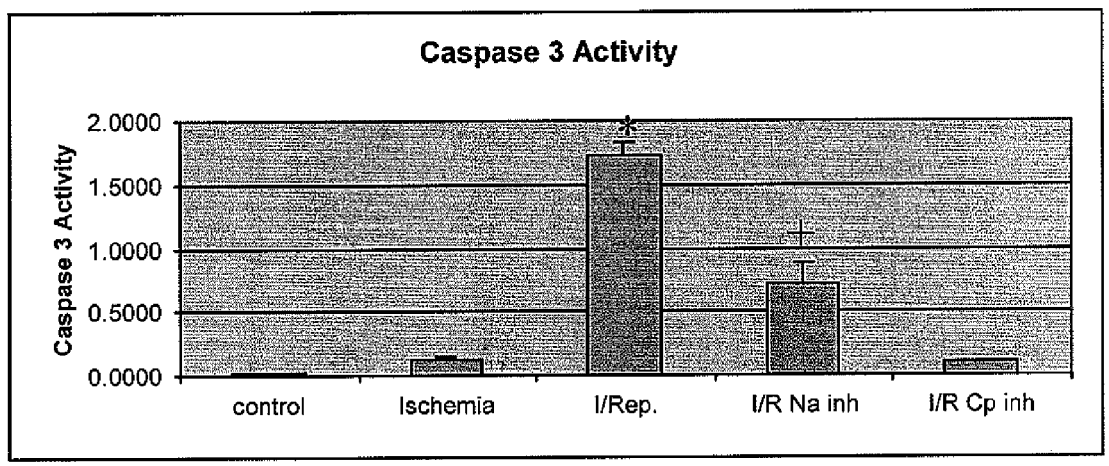
FIG. 4 shows in cultured blood-brain barrier cells that ischemia followed by reperfusion results in a significant increase in caspase 3 activity (*, $P<0.05$), that is inhibited (+, $P<0.05$) by incubating in the presence of an inhibitor (dimethylamiloride) of Na/H exchange. I/Rep is ischemia followed by reperfusion; Na inh is ischemia/reperfusion with inhibitor; I/R Cp inh is ischemia/reperfusion with specific caspase inhibitors as an internal control.

Ischemia followed by reperfusion results in a significant increase in caspase 3 activity (*, P<0.05), that is inhibited (+, P<0.05) by incubating in the presence of an inhibitor (dimethylamiloride, 100 μM) of Na/H exchange. Values are mean±SD. N=3 observations. The data shown in FIG. 4 are consistent with the hypothesis that activation of Na/H exchange during ischemia/reperfusion results in elevated intracellular calcium concentration that, in turn, initiates mitochondrial damage and caspase 3 activation. Caspase 3 activation is associated with the mitochondrial pathway for programmed cell-death (apoptosis).

Example 6

Evidence that the Antioxidants Glutathione (GSH), N-acetylcystein (NAC), and Gamma-glutamyl Cysteine (γ-Glu-Cys) Inhibit Cell Damage to Blood-brain Barrier Endothelial Cells Cultured blood-brain barrier endothelial cells were incubated under conditions of ischemia (1.5 hours) followed by reperfusion (3.0 hours), in the presence and absence of glutathione or glutathione-related antioxidants. Cellular damage was detected by measuring release of lactate dehydrogenase (LDH) into the incubation medium, following treatment. For this measurement, 50 ml of culture medium is transferred to a 96-well flat-bottomed plate, and a colorimetric assay is performed at 490 run, using a commercial kit from Promega. LDH is quantified as the percent of total cells releasing the enzyme, determined by treating reference cells with a detergent.

Figure 5:
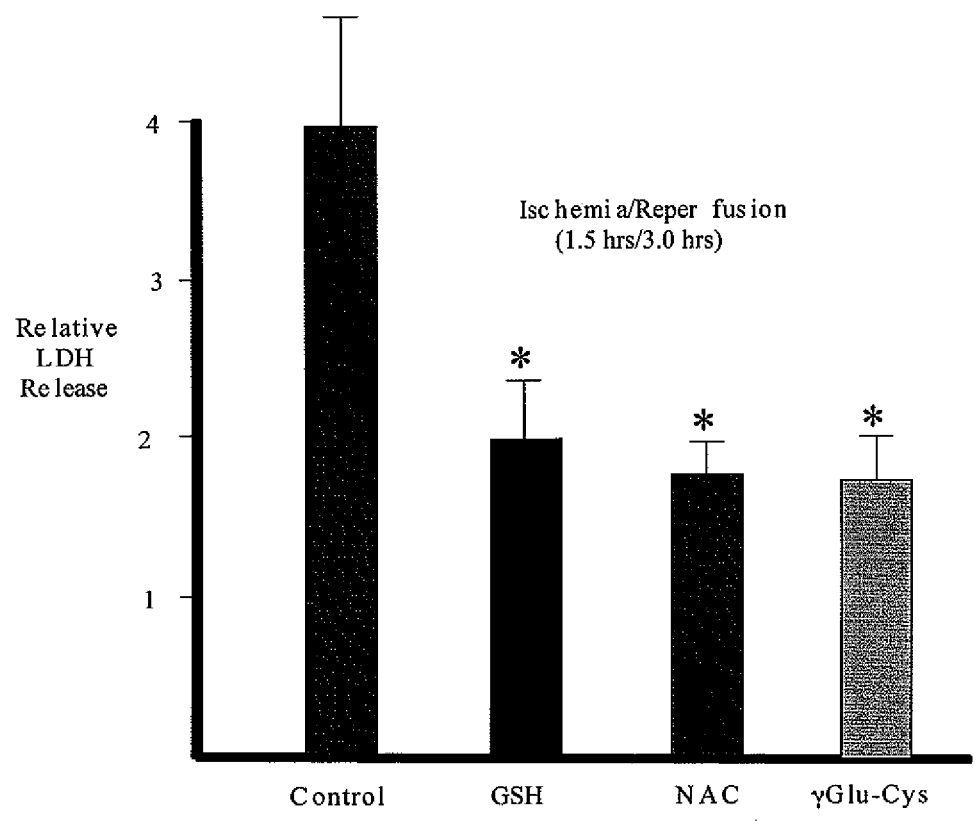
FIG. 5 is data showing that the antioxidants glutathione (GSH), N-acetylcysteine (NAC), and gamma-glutamyl cysteine (γ-Glu-Cys) inhibit cell damage to blood-brain barrier endothelial cells cultured under conditions of ischemia and reperfusion.

The data show that cellular damage was significantly reduced in the presence of native glutathione (GSH, 1 mM), N-acetylcysteine (NAC, 1 mM), and γ-glutamyl cysteine (γ-Glu-Cys, 1 mM) (FIG. 5) (*, P<0.05). Values are mean±SD. N=3 observations. The data are consistent with our proposal that glutathione-related antioxidants are useful in preventing reperfusion injury (i.e., hemorrhagic transformation) during reperfusion following ischemic stroke.

Example 7

Figure 6:
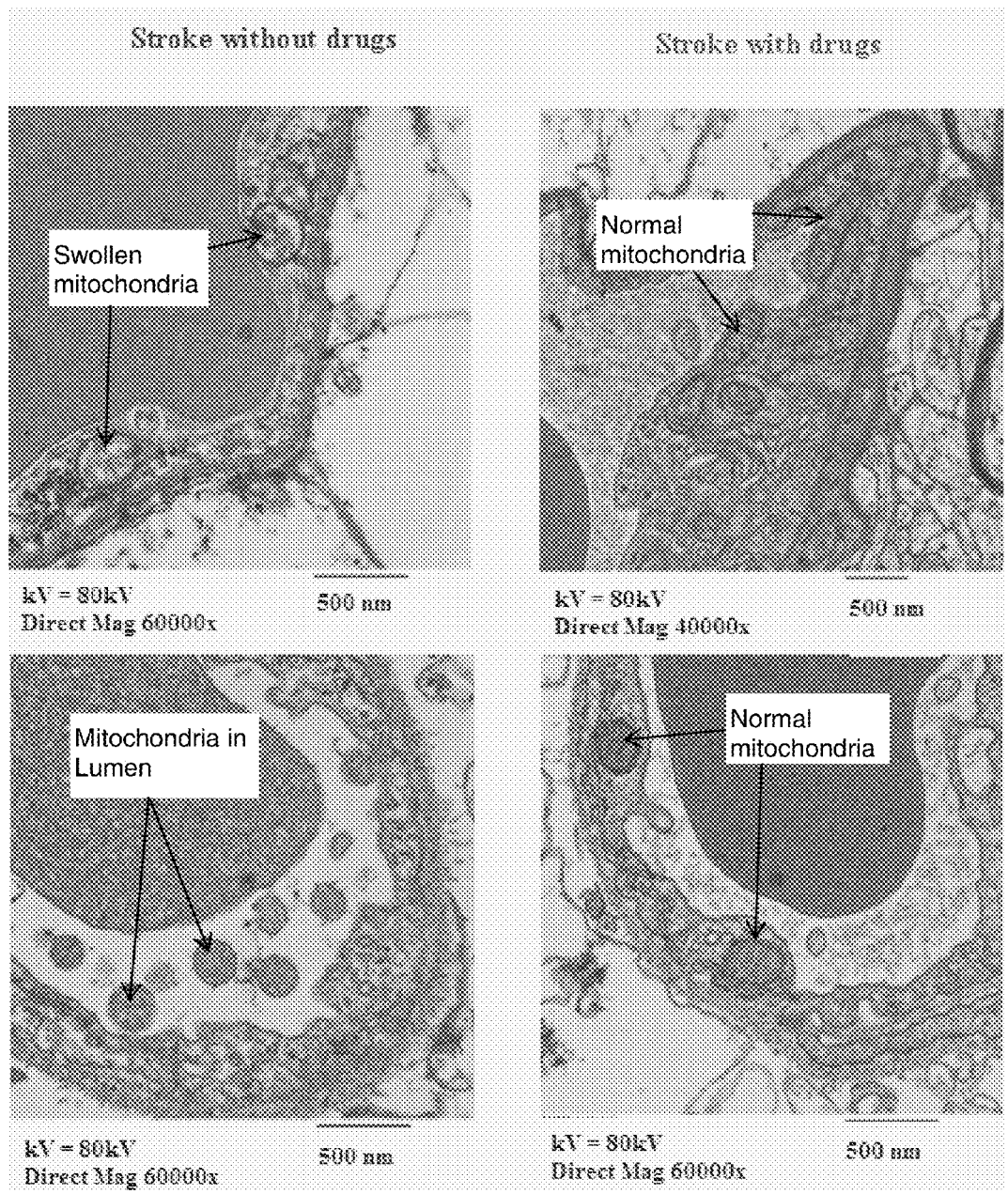
FIG. 6 illustrates the protective effects of γ-Glu-Cys and KB-R7943 to blood-brain barrier endothelial cells under conditions of transient ischemic stroke in vivo. Tissue from two representative animals given stroke without the drugs is displayed in the left panels, and shows swollen mitochondria. Tissue from two representative stroked animals that were administered the drugs at the time of reperfusion is displayed in the right panels, and shows typical mitochondria. Mitochondrial swelling is indicative of cell damage preceding apoptosis. For all animals studied, the average percent change (increase) in mitochondrial area from blood-brain barrier endothelial cells in the ipsilateral cortex (stroke) compared to the contralateral internal control is significantly greater ($P<0.0015$, 67±15 vs. 13±12 SD) when comparing animals without the drugs (N=4), versus those without the drugs (N=4).

Evidence that γ-Glu-Cys and KB-R7943 Stabilize the Blood-brain Under Conditions of Transient Ischemic Stroke In Vivo Rats are given transient ischemic strokes (1 hour ischemia, 24 hour reperfusion) using middle cerebral artery occlusion in the presence and absence of γ-Glu-Cys (antioxidant, 400 mg/Kg) and KB-R7943 (prevents rise in intracellular calcium concentration, 10 mg/Kg). Drugs are administered intravenously in buffered saline at the time of reperfusion. The ultrastructure of blood-brain barrier endothelial cells is illustrated and compared for two representative animals in FIG. 6. Brain capillaries from the ipsilateral (stroked) hemisphere are shown for animals without the drugs (left panels) and with the drugs (right panels). As can be observed, the mitochondria from blood-brain barrier endothelial cells in animals given strokes without the drugs (left panels) are swollen compared to those from stroked animals administered the drugs at the time of reperfusion. For all of the animals in this study, the average percent change (increase) in mitochondrial area from blood-brain barrier endothelial cells in the ipsilateral cortex (stroke) compared to the contralateral internal control is significantly greater (P<0.0015, 67±15 vs. 13±12 SD) when comparing animals without the drugs (N=4), versus those with the drugs (N=4). Mitochondrial swelling is an indicator of injury and the initiation of apoptosis. The data indicate that the drugs stabilize the blood-brain barrier under conditions of transient ischemic stroke.

Example 8

Figure 7:
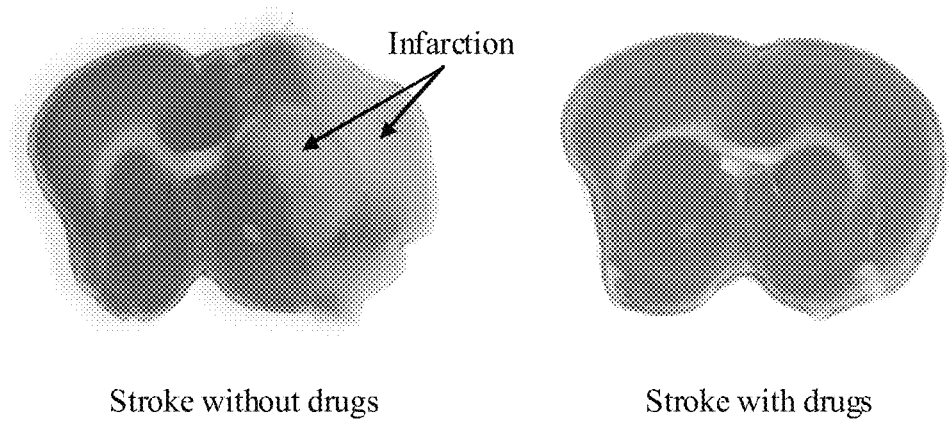
FIG. 7 are brain coronal sections taken from two representative stroked animals with and without γ-Glu-Cys and KB-R7943, illustrating the apparent protective effect of the drugs on infarction measured in vivo. The area of infarction in the stroked (ipsilateral) hemisphere is demonstrated by staining with TTC. For all of the animals studied, the average area of infarction (percent of total hemisphere) was 41.4±7.7 vs. 17.3±12.2 (mean±SEM) comparing animals without (N=4) and with (N=4) the drugs, respectively.

Evidence that γ-Glu-Cys and KB-R7943 Reduce the Area of Brain Infarction from Stroke In the same animals described in Example 7, the area of infarction in the stroked (ipsilateral) hemisphere is demonstrated by staining with TTC. Infarction is compared in coronal sections taken from stroked animals with and without γ-Glu-Cys and KB-R7943. The findings for two representative animals are illustrated in FIG. 7. For all of the animals is this study, the average area of infarction (percent of total hemisphere) was 41.4±7.7 vs. 17.3±12.2 (mean±SEM) comparing stroked animals (N=4) without and with the drugs, respectively.

Example 9

Evidence that γ-Glu-Cys and KB-R7943 Protect Against Neurological Deficits When Administered at the Time of Reperfusion Following Transient Ischemia (Table 1)

TABLE 1 summarizes the effects of treatment of stroked animals with γ-Glu-Cys and KB-R7943 on neurological behavior. An apparent neuroprotective effect of the drugs is observed when administered at the time of reperfusion, following transient ischemia. This data is from the same animals described in Examples 7 and 8. TABLE-US-00001 TABLE 1 Stroked animals without drugs: 1. Right front paw deficit 2. Slow moving, with some torticolis 3. Obvious paresis 4. Obvious paresis Two additional animals died following stroke. Stroked animals with drugs 5. No observable deficits 6. No observable deficits 7. No observable deficits 8. Displays some motor deficits No deaths following stroke While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

REFERENCES

The National Institute of Neurological Disorders and Stroke rt-PA Stroke Study Group. Tissue plasminogen activator for acute ischemic stroke. N Engl J Med 333: 1581-1587, 1995.

Abbruscato T J and Davis T P. Combination of hypoxia/aglycemia compromises in vitro blood-brain barrier integrity. J Pharmacol Exp Ther 289: 668-675, 1999.

Anderson M E. Glutathione and glutathione delivery compounds. In: Advances in Pharmacology. New York: Academic Press, 1997, p. 65-78.

Audus K L, Rose J M, Wang W, and Borchardt R. Brain microvessel endothelial cell culture systems. In: Introduction to the Blood-Brain Barrier, edited by Pardridge W M. Cambridge: Cambridge University Press, 1998, p. 86-93.

Betz A L, Firth J A, and Goldstein G W. Polarity of the blood-brain barrier: distribution of enzymes between the luminal and antiluminal membranes of brain capillary endothelial cells. Brain Res 192: 17-28, 1980.

Beuckmann C T and Galla Tissue culture of brain endothelial cells-induction of blood-brain barrier properties by brain factors. In: Introduction to the blood-brain barrier, edited by Pardridge W M. Cambridge: Cambridge University Press, 1998, p. 79-85.

Bradbury M. The Concept of a Blood-Brain Barrier. New York: John Wiley and Sons, 1979.

Bradbury M W B. The blood-brain barrier. Transport across the cerebral endothelium. Circ Res 57: 213-222, 1985.

DeBault L E. γ-glutamyl transpeptidase induction mediated by glial foot process-to-endothelium contact in co-culture. Brain Res 220: 432-435, 1981.

DeKeyser J, Sulter G, and Luiten P G. Clinical trials with neuroprotective drugs in acute ischaemic stroke: are we doing the tight thing? Trends Neurosci 22: 535-540, 2001.

Del Zoppo G J, Von Kummer R, and Hammann G F. Ischaemic damage of brain microvessels: inherent risks for thrombolytic treatment in stroke. J Neural Neurosurg Psychiatry 65: 1-9, 1998.

Gartshore G, Patterson J, and Macrae I M. Influence of ischemia and reperfusion on the course of brain tissue swelling and blood-brain barrier permeability in a rodent model of transient focal cerebral ischemia. Exp Neurol 147: 353-360, 1997.

Halestrap A P. The mitochondrial permeability transition: its molecular mechanism and role in reperfusion injury. Biochem Soc Symp 66: 181-203, 1999.

Ikeda K, Nagashima T, Wu S, Yamaguchi M, and Tamaki N. The role of calcium ion in anoxia/reoxygenation damage of cultured brain capillary endothelial cells. Acta Neuochir Suppl (Wien) 70: 4-7, 1997.

Iwamoto T, Watano T, and Shigekawa M. A novel isothiourea derivative selectively inhibits the reverse mode of Na/Ca exchange in cells expressing NCX1. J Biol Chem 271: 22391-22397, 1996.

Kuro T, Kobayashi Y, Takaoka M, and Matsumura Y. Protective effect of KB-R7943, a novel Na/Ca exchange inhibitor, on ischemic acute renal failure in rats. J Pharmacol 81: 247-251, 1999.

Kuroiwa T, Shibutani M, and Okeda R. Blood-brain barrier disruption and exacerbation of ischemic brain edema after restoration of blood flow in experimental focal cerebral ischemia. Acta Neuropathol 76: 62-70, 1988.

Mayer B and Oberbauer R. Mitochondrial regulation of apoptosis. NIPS 18: 89-94, 2003.

Meresse S, Dehouck M-P, Delmore P, Bensaid M, Tauber J-P, Delbart C, Fruchart J-C, and Cecchelli R. Bovine brain endothelial cells express tight junctions and monoamine oxidase activity in long-term culture. J Neurochem 53: 1363-1371, 1989.

Muruganandam A, Smith C, Ball R, Herring T, and Stanimirovic D. Glutathione homeostasis and leukotriene-induced permeability in human blood-brain barrier endothelial cells subjected to in vitro ischemia. Acta Neurochir Suppl 76: 29-34, 2000.

Nakamura A, Harada K, Sugimoto H, Nakajima F, and Nishimura N. Effects of KB-R7943, a novel Na/Ca inhibitor, on myocardial ischemia/reperfusion injury. Folia Pharmacol Jpn 111: 105-115, 1998.

Orrenius S, Ankarcrona M, and Nicotera P. Mechanisms of calcium-related cell death. Adv Neural 71: 137-151, 1996.

Peterson D R, Rambow J, Sukowski E J, and Zikos D. Glutathione transport by the blood-brain barrier. FASEB J 13: A709, 1999.

Reese T S and Karnovsky M J. Fine structural localization of a blood-brain barrier to exogenous peroxidase. J Cell Bial 34: 207-217, 1967.

Rosenberg G A. Matrix metalloproteinases in neuroinflammation. Glia 39: 279-291, 2002.

Rosenberg G A, Estrada E Y, and J. E. D. Matrix metalloproteinases and TIMPs are associated with blood-brain barrier opening after reperfusion in rat brain. Stroke 29: 2189-2195, 1998.

Rubin L L, Hall D E, Porter S, Barbu K, Cannon C, Homer H C, Janatpour M, Liaw C W, Manning K, Morales J, Tanner L I, Tomaselli K J, and Bard F. A cell culture model of the blood-brain barrier. J Cell Biol 115: 1725-1735, 1991.

Sun D, Lytle C, and O'Donnell M. Astroglial cell-induced expression of Na—K—Cl cotransporter in brain microvascular endothelial cells. Am J Physiol 269: C1506-C1512, 1995.

Todd N V, Picozzi P, Crockard H A, and Russell R W R. Reperfusion after cerebral ischaemia: influence of duration of ischaemia. Stroke 17: 460-466, 1986.

Tsukamoto T and Nigam S K. Tight junction proteins form large complexes and associate with the cytoskeleton in an ATP depletion model for reversible junction assembly. J Biol Chem 272: 16133-16139, 1997.

I claim:

1. A kit for reducing cerebral bleeding caused by hemorrhagic transformation following reperfusion injury caused by ischemic stroke in a mammalian subject comprising a container of an effective amount of γ-glutamyl cysteine, a container of an effective amount of 2-[2-[4-(4-nitrobenzyloxy)phenyl]ethyl]isothiourea methanesulphonate (KB-R7943) and instructions for co-administering them to the subject after the subject has had an ischemic stroke and immediately prior to administering a thrombolytic agent to the subject.

2. The kit of claim 1, wherein the thrombolytic agent is tissue plasminogen activator (tPA) or urokinase.

3. The kit of claim 1, wherein the mammalian subject is a human.

4. The kit of claim 1, wherein the γ-glutamyl cysteine is capable of reducing reactive oxygen species.

5. The kit of claim 1, wherein the instructions include the step of administering to the subject the γ-glutamyl cysteine by intravenous injection.

6. The kit of claim 1, wherein the instructions include the step of administering to the subject the γ-glutamyl cysteine at a dose of about 400 mg/Kg.

7. The kit of claim 1, wherein the instructions include the step of administering to the subject the γ-glutamyl cysteine over a period of about one minute.

8. The kit of claim 1, wherein the instructions include the step of administering to the subject the KB-R7943 at a dose of 10 mg/Kg.

9. A kit for reducing cerebral bleeding caused by hemorrhagic transformation following reperfusion injury caused by ischemic stroke in a mammalian subject comprising a container of an effective amount of γ-glutamyl cysteine, a container of an effective amount of 2-[2-[4-(4-nitrobenzyloxy)phenyl]ethyl]isothiourea methanesulphonate (KB-R7943), a syringe, and instructions for co-administering them to the subject after the subject has had an ischemic stroke and immediately prior to administering a thrombolytic agent to the subject.

* * * * *